United States Patent
Mitchell (10) Patent No.: US 10,512,747 B2
(45) Date of Patent: Dec. 24, 2019

(54) GAS OUTLET EXTENDER

(71) Applicant: Amico Interiors Corporation, Richmond Hill (CA)

(72) Inventor: Charles Henry Kingscott Mitchell, Thornhill (CA)

(73) Assignee: AMICO INTERIORS CORPORATION, Richmond Hill (CA)

( * ) Notice: Subject to any disclaimer, the term of this patent is extended or adjusted under 35 U.S.C. 154(b) by 366 days.

(21) Appl. No.: 15/272,939

(22) Filed: Sep. 22, 2016

(65) Prior Publication Data

US 2018/0080581 A1 Mar. 22, 2018

(51) Int. Cl.
*A61M 16/08* (2006.01)
*A61M 39/10* (2006.01)
*F16L 41/00* (2006.01)

(52) U.S. Cl.
CPC ......... *A61M 16/0833* (2014.02); *A61M 39/10* (2013.01); *F16L 41/00* (2013.01)

(58) Field of Classification Search
CPC ......... F16L 37/60; F16L 41/00; F16L 41/021; F16L 41/001; F16L 41/08; F17D 1/02; A16M 39/10; A16M 16/0833
USPC ............. 285/206, 12, 93, 24, 189, 205, 201, 285/133.11, 142.1, 140.1, 137.11, 136.1, 285/124.3, 19, 123.6
See application file for complete search history.

(56) References Cited

U.S. PATENT DOCUMENTS

| | | | | |
|---|---|---|---|---|
| 2,656,784 A * | 10/1953 | Benson | .................... | F16L 41/08 454/367 |
| 3,544,257 A * | 12/1970 | Cranage | .................. | F16L 41/00 137/360 |
| 3,643,985 A * | 2/1972 | Cranage | ................ | F16L 37/084 285/189 |
| 4,718,699 A * | 1/1988 | Kulish | ................. | A61G 13/107 285/12 |
| 5,197,511 A * | 3/1993 | Kohn | ....................... | F16L 37/60 137/269 |
| 5,513,966 A * | 5/1996 | Krohn | ..................... | F04B 23/04 285/24 |
| 5,562,121 A * | 10/1996 | Hodges | ................... | F16L 37/60 137/360 |
| 5,975,590 A * | 11/1999 | Cowan | .................... | F16L 13/02 285/133.11 |
| 6,189,560 B1 * | 2/2001 | Reynolds | ................ | F16L 37/60 137/329.1 |
| 6,347,643 B1 * | 2/2002 | Cope, III | ............... | F16L 37/60 137/329.1 |
| 6,438,895 B1 * | 8/2002 | Fortier | ................... | A01G 23/14 285/133.11 |
| 6,655,925 B1 * | 12/2003 | Robenalt | ................ | F04B 35/06 137/557 |

(Continued)

*Primary Examiner* — Anna M Momper
*Assistant Examiner* — William S. Choi
(74) *Attorney, Agent, or Firm* — Ridout & Maybee LLP (57) ABSTRACT

A gas outlet extender allows for relocation of existing medical gas outlets to positions that are more ergonomic to care-givers at the point-of-use. In various aspects, the gas outlet extender may take one source of gas supply and provide the facility with a plurality of separate sources of that gas supply. By taking measurements of various parameters of the gas supply, an installer may obtain confidence that the gas flow for each of the plurality of separate sources meets regulatory requirements.

12 Claims, 7 Drawing Sheets

(56) References Cited

U.S. PATENT DOCUMENTS

| | | | | |
|---|---|---|---|---|
| 7,648,175 B2* | 1/2010 | Hough | ............... | F16M 11/22 |
| | | | | 137/329.4 |
| 8,555,913 B2* | 10/2013 | Stinson | ............... | F16L 5/02 |
| | | | | 137/360 |
| 8,707,989 B2* | 4/2014 | Pucciani | ............... | F16L 3/16 |
| | | | | 137/561 A |
| 8,807,601 B2* | 8/2014 | Anderson | ............... | F16L 5/06 |
| | | | | 285/139.2 |
| 2018/0320809 A1* | 11/2018 | Kawasaki | ............... | F16L 41/03 |

\* cited by examiner

GAS OUTLET EXTENDER

FIELD

The present application relates generally to outlets and, more specifically, to a gas outlet extender.

BACKGROUND

Unfortunately, outlets, whether for gases or for electricity, are not always in a location that is convenient for use by a device in the service of a patient.

BRIEF DESCRIPTION OF THE DRAWINGS

Reference will now be made, by way of example, to the accompanying drawings, which show example implementations; and in which.

DETAILED DESCRIPTION

A gas outlet extender allows for relocation of existing medical gas outlets to positions that are more ergonomic to care-givers at the point-of-use. In various aspects, the gas outlet extender may take one source of gas supply and provide the facility with a plurality of separate sources of that gas supply. By taking measurements of various parameters of the gas supply, an installer may obtain confidence that the gas flow for each of the plurality of separate sources meets regulatory requirements.

According to an aspect of the present disclosure, there is provided gas outlet extender for use with a primary gas outlet back body. The gas outlet extender includes a mounting plate defining an aperture, the mounting plate having a first side and a second side, an outlet extender insertion element, on the first side of the mounting plate, defining an insertion element channel for a flow of gas to or from the primary gas outlet back body and a distributer, on the second side of the mounting plate, the distributer having a tap having a tap channel, the distributer connected to the insertion element through the aperture and defining a distributer channel for a flow of gas between the insertion element channel and the tap channel.

Other aspects and features of the present disclosure will become apparent to those of ordinary skill in the art upon review of the following description of specific implementations of the disclosure in conjunction with the accompanying figures.

Figure 1:
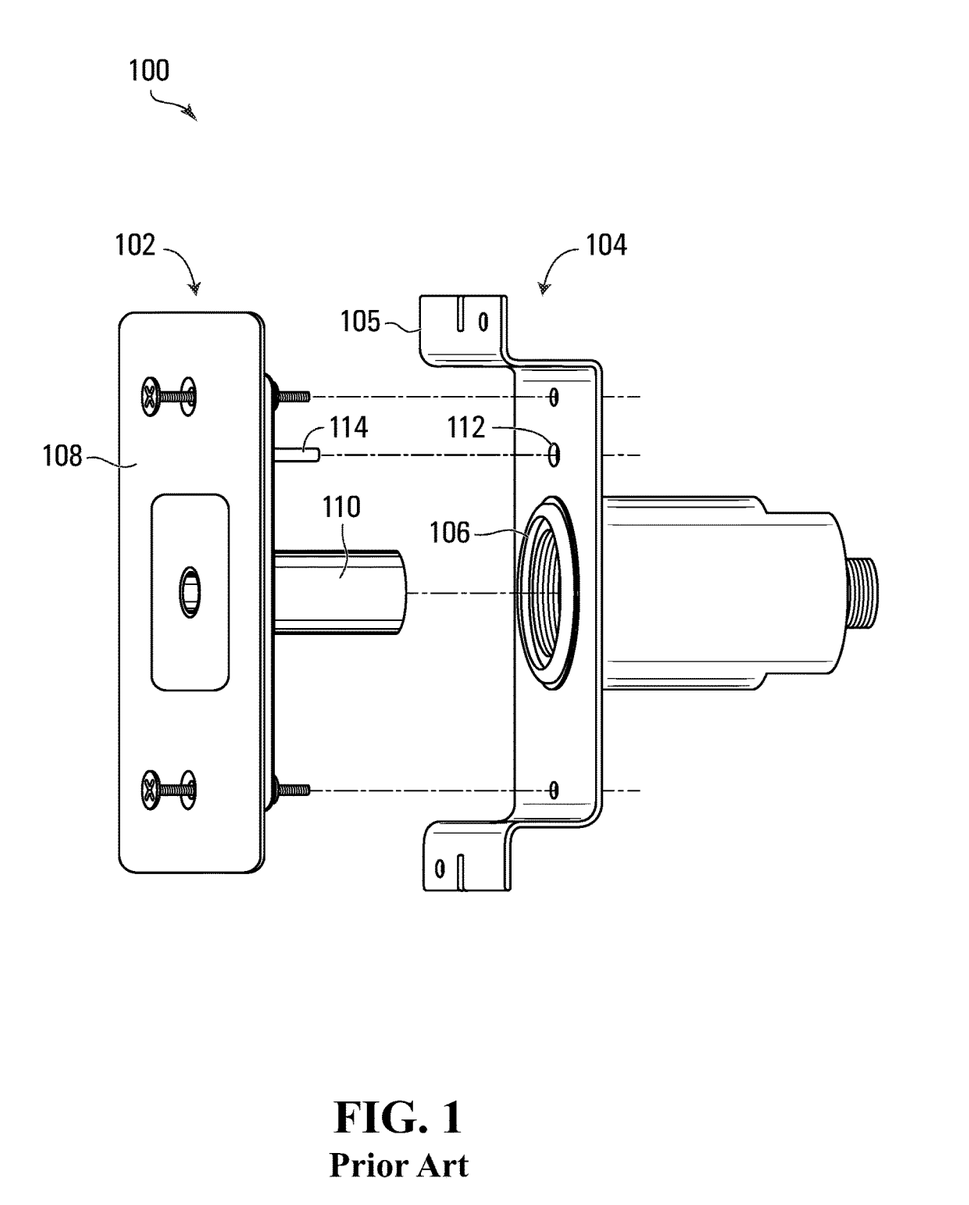
FIG. 1 illustrates a prior art gas outlet including a front body and a back body.

A prior art medical gas outlet 100 is illustrated in FIG. 1 as having two bodies: a front body 102; and a back body 104. The back body 104 is installed in an aperture in a wall (not shown) and maintains a connection to a source of medical gas (not shown). The medical gas may be, for just five examples among many, oxygen, nitrous oxide, nitrogen or medical (i.e., filtered, clean) air. The medical gas may also be a medical vacuum. That is, rather than a source of gas, the outlet can serve as a sink for a gas or a mix of gasses, such as air. The back body 104 defines a port 106. The front body 102 features a faceplate 108. Conveniently, the faceplate 108 identifies the gas that is supplied via the back body 104. The front body 102 also includes a front body cylinder 110. The back body 104 includes a back body plate 105 that defines a gas-specific aperture 112. The front body 102 includes a front body gas-specific pin 114 that is arranged to be received by the gas-specific aperture 112.

In prior art operation, the front body cylinder 110 is received by the port 106 defined in the back body 104 so as to make a fluid connection to the gas source supplied to the back body 104.

Notably, the front body cylinder 110 is cylindrical only because that is the shape that readily received by the port 106 defined in the back body 104. More generically, the front body cylinder may be called a front body insertion element 110.

The front body insertion element 110 defines an insertion element channel (not specifically shown) for a flow of gas to or from the gas outlet back body 104 as facilitated by retention of the front body insertion element 110 within the port 106.

As may be readily understood, a supply of medical gas may be provided from behind the wall. The prior art medical gas outlet 100 and, in particular, the front body 102 provides a straightforward access point for the medical gas. As is typical, the front body 102 includes an industry-standard port to allow for a device that is to employ the medical gas to connect to the front body 102 and, thereby, have access to the medical gas supplied to the back body 104.

The gas-specific aperture 112, by standard, ensures that, for example, a front body with a faceplate that is labeled "Nitrogen" may not be connected to a back body supplied with oxygen.

Figure 2:
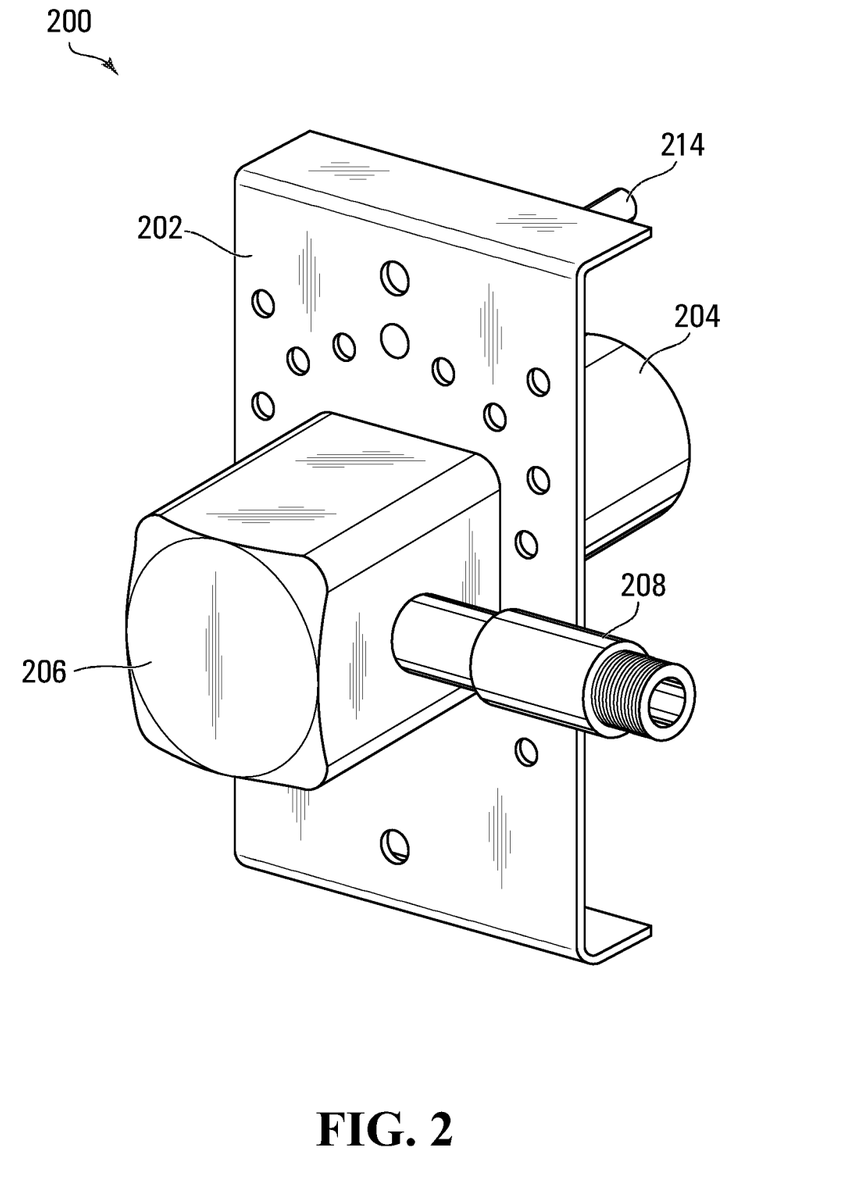
FIG. 2 illustrates a single-tap gas outlet extender in accordance with aspects of the present application.

FIG. 2 illustrates a gas-specific outlet extender 200. The outlet extender 200 includes an outlet extender plate 202. On the side of the outlet extender plate 202 that, in operation, faces the back body 104, the outlet extender 200 includes an outlet extender insertion element 204 and an outlet extender gas-specific pin 214.

Notably, the outlet extender insertion element 204 is cylindrical only because that is the shape that readily received by the port 106 defined in the back body 104. The outlet extender insertion element 204 may be called the outlet extender cylinder 204.

The outlet extender cylinder 204 defines an outlet extender insertion element channel (not specifically shown) for a flow of gas to or from the gas outlet back body 104 as facilitated by retention of the outlet extender insertion element 204 within the port 106.

On the side of the outlet extender plate 202 that, in operation, faces away from the back body 104, the outlet extender 200 includes a distributer 206. As illustrated in FIG. 2, the distributer 206 includes a single tap 208. The tap 208 defines a tap channel. The distributer 206 defines a distributer channel (not specifically shown). The distributer channel allows for a flow of gas between the insertion element channel in the outlet extender insertion element 204 and the tap channel in the tap 208.

The distributer 206 connects with the outlet extender insertion element 204 through an aperture (not shown) in the outlet extender plate 202. Indeed, the distributer 206 and the outlet extender insertion element 204 may be formed integrally.

Figure 3:
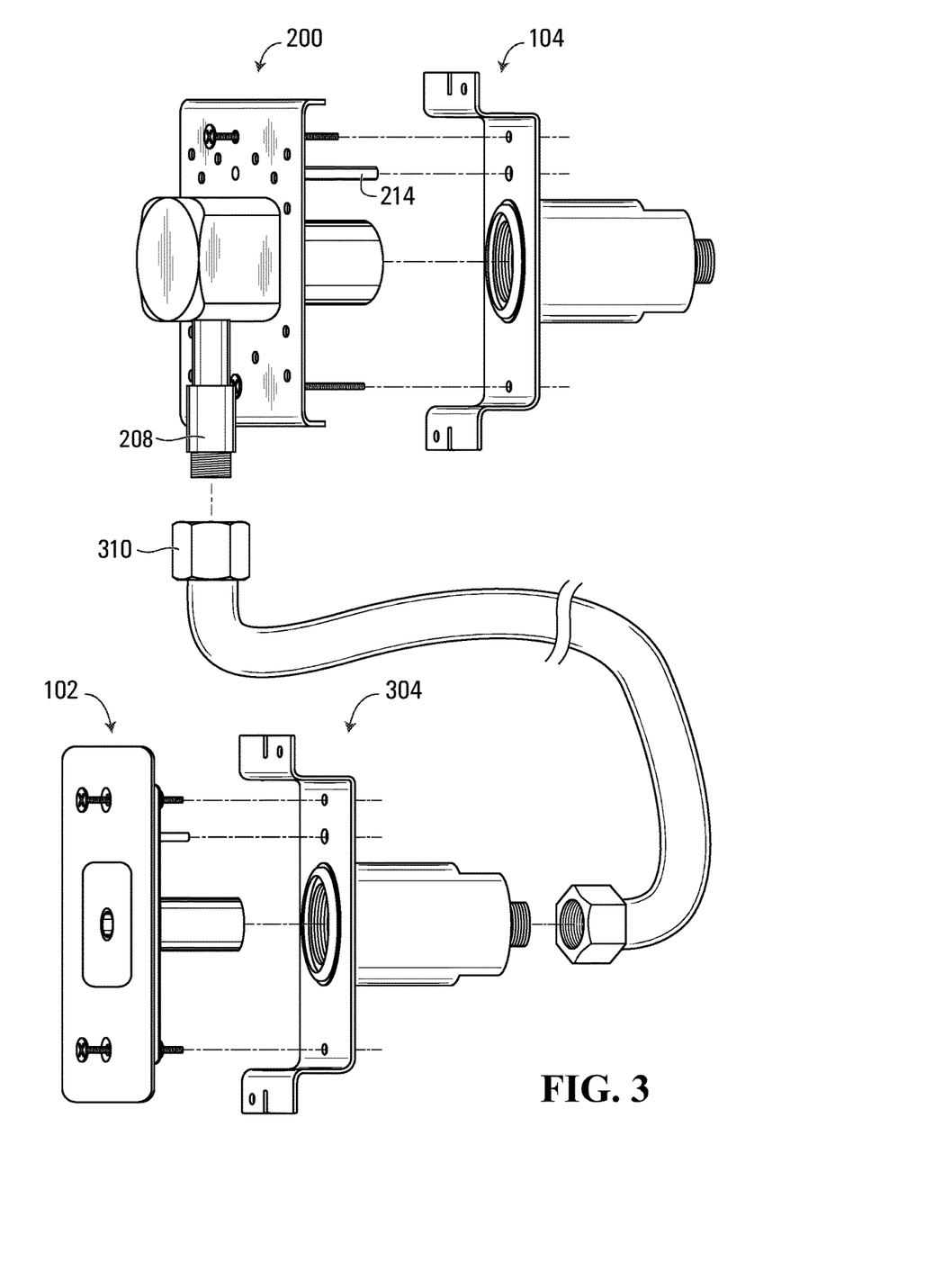
FIG. 3 illustrates the gas outlet extender of FIG. 2 in context with the front body and back body of FIG. 1 and a secondary back body in accordance with aspects of the present application.

FIG. 3 illustrates the gas outlet extender 200 of FIG. 2 in context with the front body 102 and the back body 104 of FIG. 1. For the purposes of FIG. 3, the back body 104 may be called the primary back body 104. FIG. 3 further illustrates a secondary back body 304 and a connector 310 for fluidly connecting the tap 208 on the gas outlet extender 200 to the secondary back body 304. For reasons that will be understood by those of ordinary skill in the art, the type, or gas-specific nature, of the secondary back body 304 is the same as the type of the primary back body 104. For example, the back body plate 105 has the gas-specific aperture 112 in a gas-specific location, arranged to mate with the front body gas-specific pin 114 mounted to the front body 102. Similarly, a back body plate for the secondary back body 304 should also have a gas-specific aperture in the same gas-specific location. Accordingly, a connection will be allowed between the front body 102 and the secondary back body 304.

Conveniently, the outlet extender gas-specific pin 214 of the gas outlet extender 200 ensures that the gas outlet extender 200 may only be received by the primary back body 104 that supplies the gas for which the gas outlet extender 200 was designed. As illustrated in FIG. 3, the connector 310 is implemented as a hose. As an alternative to the hose, the connector 310 may be implemented in copper piping. Furthermore, the connector 310 may be color-coded, labeled or festooned with some indication of the gas with which the connector 310 is to be associated.

Figure 4:
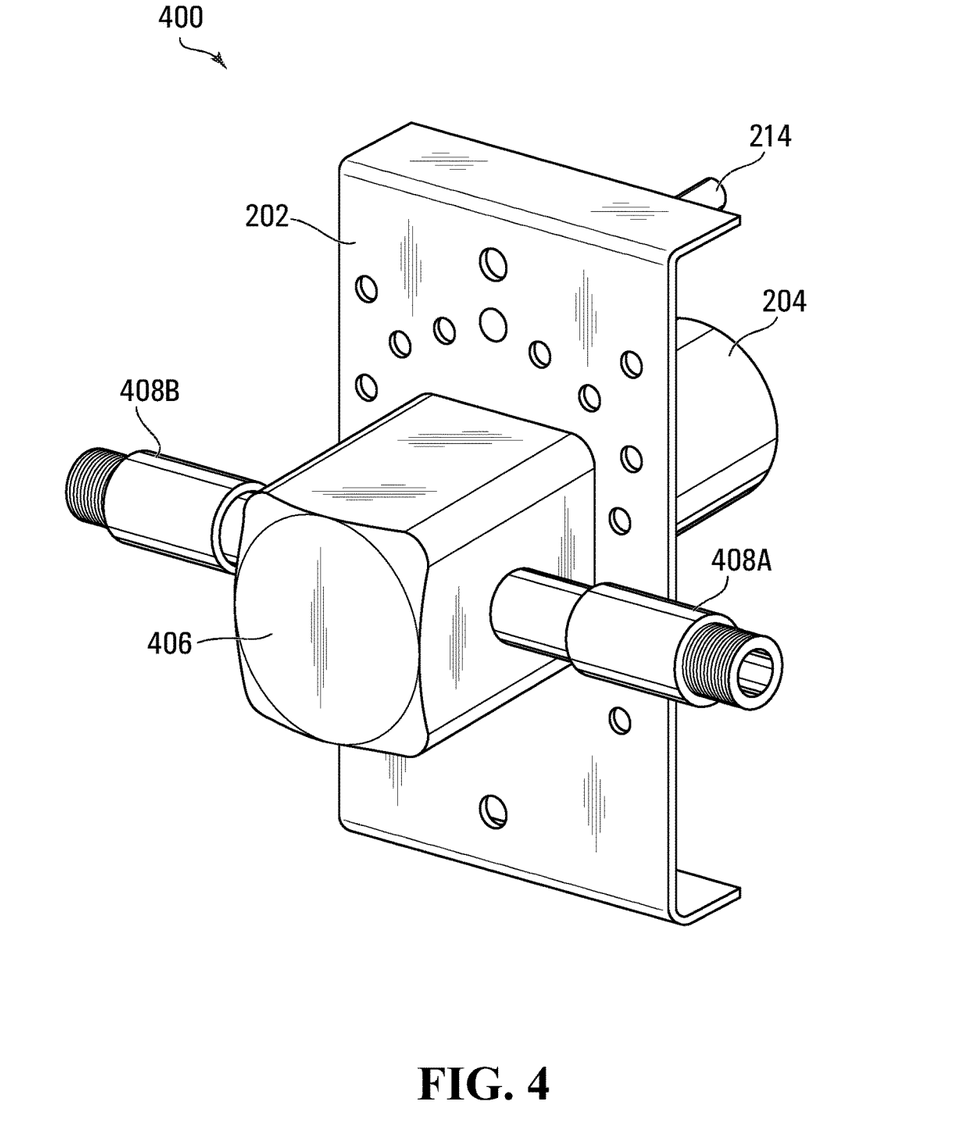
FIG. 4 illustrates a double-tap gas outlet extender in accordance with aspects of the present application.

An alternative design for the gas outlet extender 200 is illustrated in FIG. 4. FIG. 4 illustrates a double-tap gas outlet extender 400. The double-tap gas outlet extender 400 includes many of the components of the gas outlet extender 200 of FIG. 2, such as the outlet extender plate 202, the outlet extender cylinder 204 and the outlet extender gas-specific pin 214. The double-tap gas outlet extender 400 features a distinct double-tap distributer 406 with a first tap 408A and a second tap 408B.

Each of the taps 408A, 408B defines a respective tap channel. The double-tap distributer 406 defines a plurality of distributer channels (not specifically shown). The plurality of distributer channels allow for a flow of gas between the insertion element channel in the outlet extender insertion element 204 and the respective tap channels in the taps 408A, 408B.

Figure 5:
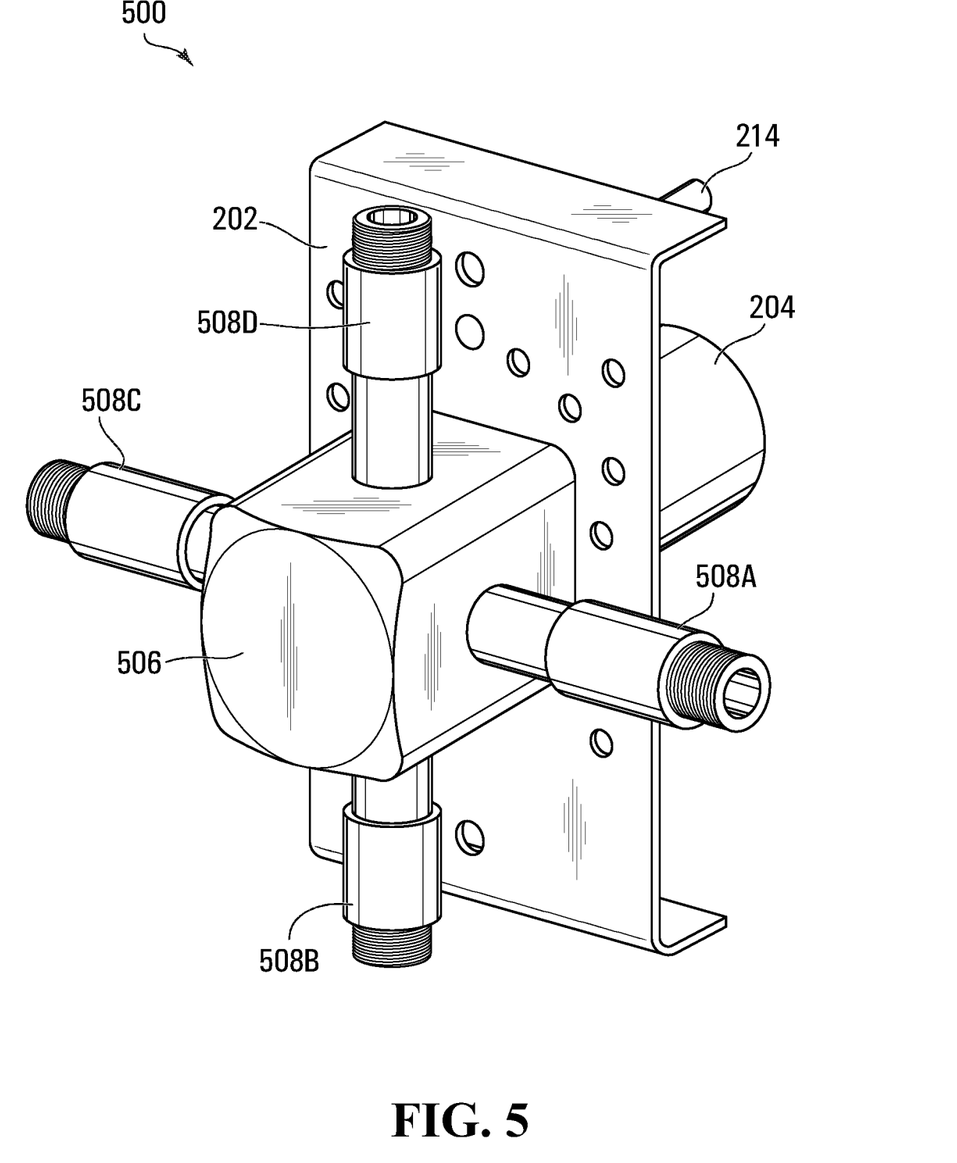
FIG. 5 illustrates a quadruple-tap gas outlet extender in accordance with aspects of the present application.

A further alternative design for the gas outlet extender 200 is illustrated in FIG. 5. FIG. 5 illustrates a quadruple-tap gas outlet extender 500. The quadruple-tap gas outlet extender 500 includes many of the components of the gas outlet extender 200 of FIG. 2, such as the outlet extender plate 202, the outlet extender cylinder 204 and the outlet extender gas-specific pin 214. The quadruple-tap gas outlet extender 500 features a distinct quadruple-tap distributer 506 with a first tap 508A, a second tap 508B, a third tap 508C and a fourth tap 508D.

Each of the taps 508A, 508B, 508C, 508D defines a respective tap channel. The quadruple-tap distributer 506 defines a plurality of distributer channels (not specifically shown). The plurality of distributer channels allow for a flow of gas between the insertion element channel in the outlet extender insertion element 204 and the respective tap channels in the taps 508A, 508B, 508C, 508D.

Unfortunately, the prior art medical gas outlet 100 (including the front body 102 and the primary back body 104) is not always in a location that is convenient for use by the device in the service of a patient.

In overview, an outlet relocation assembly is proposed herein. The outlet relocation assembly (see FIG. 3 and, in particular, the outlet extender 200, the connector 310 and the secondary back body 304) allows for relocation of the prior art medical gas outlet 100 (more particularly, it is the front body 102 that is relocated) to a position that is more convenient to care-givers at the point-of-use.

The outlet relocation assembly according to aspects of the present application may be installed within a framework that supports the secondary back body 304.

Figure 6:
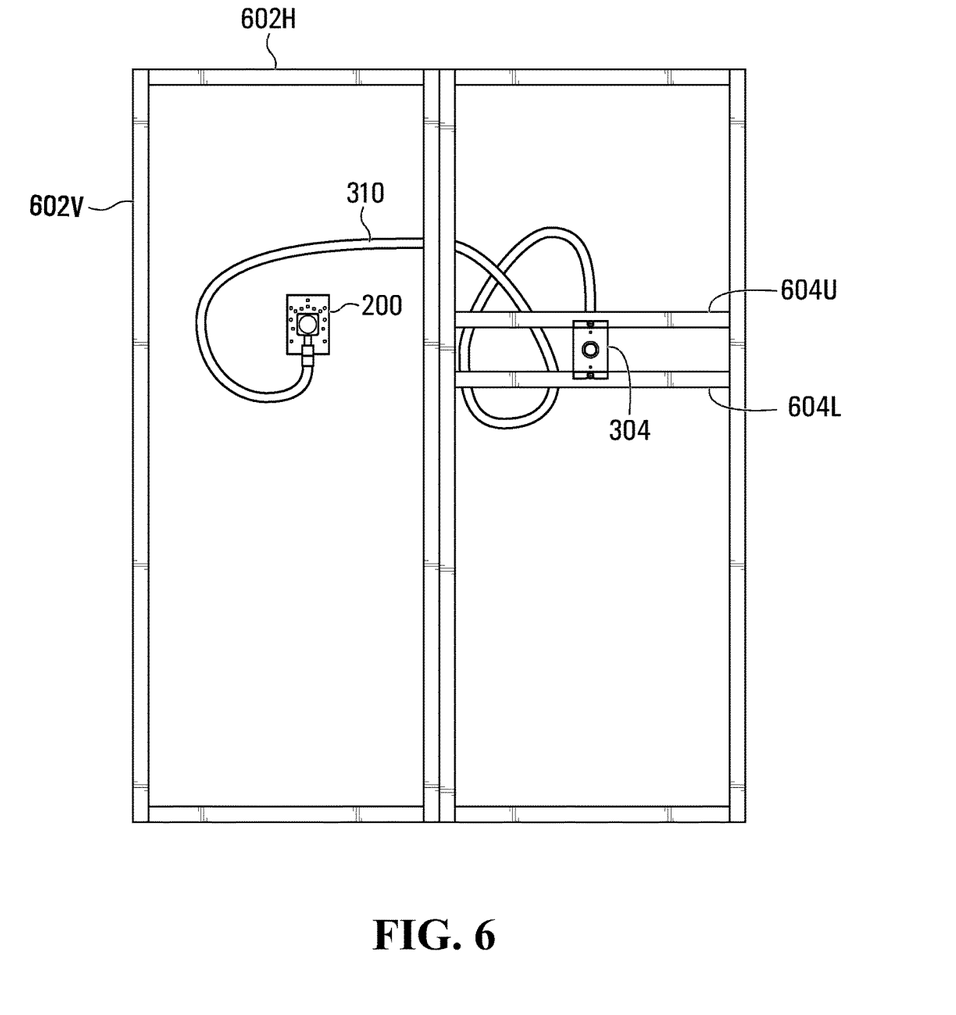
FIG. 6 illustrates the gas outlet extender of FIG. 2 in context with the secondary back body of FIG. 3 mounted to a framework in accordance with aspects of the present application.

The framework may, in one instance, be formed from extruded 6063 T5 aluminum alloy. As illustrated in FIG. 6, the framework may include vertical components 602V connected to horizontal components 602H. Connection of the components to each other is expected to be carried out in a conventional manner.

Furthermore, the framework may include one or more outlet support arms, such as an upper outlet support arm 604U and a lower outlet support arm 604L, to support the secondary back body 304.

The framework 602V, 602H may be placed against the wall in which the prior art medical gas outlet 100 has been previously installed.

Figure 7:
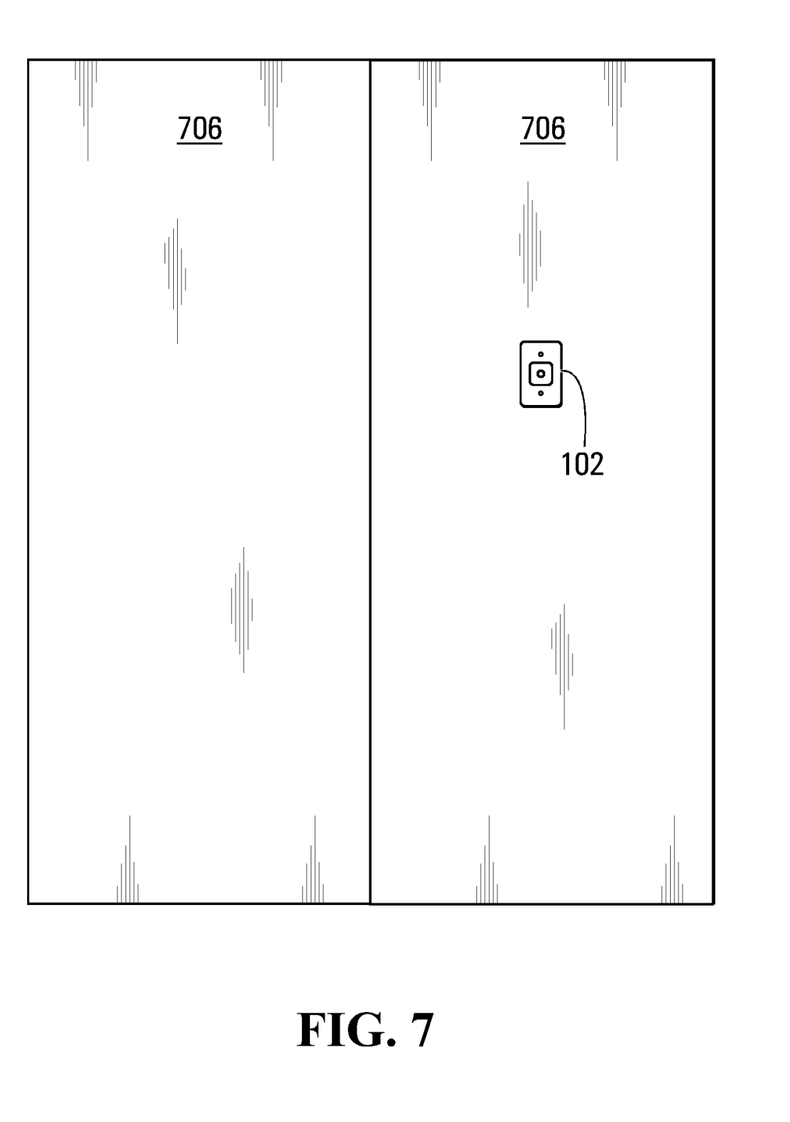
FIG. 7 illustrates the front body of FIG. 1 mounted in an aperture in a panel fastened to the framework of FIG. 6 in accordance with aspects of the present application.

FIG. 7 illustrates the framework 602V, 602H of FIG. 6 covered with a plurality of removable panels 706. One of the panels 706 includes an aperture (not specifically shown) with a size and location corresponding to the secondary back body 304 so that the front body 102 may be installed in the aperture.

Indeed, the framework, with the panels 706 installed, acts to hide the primary back body 104 from view.

The outlet extender 200 in combination with the connector 310 may be designed to maximize flow and minimize pressure drop for a specific gas from the primary back body 104 to the secondary back body 304.

In operation, once the framework 602V, 602H has been properly positioned, the outlet extender 200 has been connected to the primary back body 104 and the connector 310 has been used to fluidly connect the tap 208 on the gas outlet extender 200 to the secondary back body 304, panels 706 may be installed. The panels 706 are fastened to the framework 602V, 602H. The fastening of the panels 706 to the framework 602V, 602H is expected to be carried out in a conventional manner. Subsequent to the fastening of the panels 706 to the framework 602V, 602H, the front body 102 may be installed in fluid communication with the secondary back body 304.

Once the outlet relocation assembly has been assembled, the front body 102 connected to the secondary back body 304 may be used in the service of patients (that is, equipment may be attached to the front body 102 in a conventional manner) as if the front body 102 was directly connected to the primary back body 104.

Conveniently, the panels 706 may be configured to be removable to, thereby, allow access to the outlet extender 200 for scheduled maintenance as required by the known National Fire Protection Association Health Care Facilities Code (NFPA).

The 2015 edition NFPA 99: Health Care Facilities Code provides performance criteria for health care facilities that builds on the risk-based approach introduced in the 2012

NFPA 99, where it is the risk posed to patients and staff, not the type of building, that defines safety guidelines. Provisions govern installation, inspection, testing, maintenance, performance, and safe practices for facilities, material, equipment, and appliances—including medical gas and vacuum systems formerly found in NFPA 99C*.

As may be noted from FIGS. 4 and 5, outlet extender designs are contemplated with multiple taps. Before employing a multiple-tap outlet extender with corresponding primary, secondary, etc. connectors with corresponding secondary, tertiary, etc. back bodies and corresponding primary, secondary, etc. front bodies, it behooves an installer to determine whether the conditions under which the prior art medical gas outlet 100 operates may be duplicated. To that end, the installer may obtain measurements of various parameters associated with the operation of the prior art medical gas outlet 100. Many of such parameters will be understood to be directly associated with the supply of the gas to the primary back body 104. Example parameters include those parameters related to gas flow rate, pressure drop, gas restrictions and temperature compensation. Through a review of these parameters, the installer may determine how many taps may be supported on the outlet extender that is installed in the primary back body 104 and, accordingly, how many relocated outlets can be added. Through the review of these parameters, the installer may also determine the length of the connector 310 that can be used and, hence, a permissible distance between the outlet extender and each relocated outlet.

By taking measurements of various parameters of the gas supply, an installer may obtain confidence that the gas flow for each of the plurality of separate sources meets regulatory requirements.

The above-described implementations of the present application are intended to be examples only. Alterations, modifications and variations may be effected to the particular implementations by those skilled in the art without departing from the scope of the application, which is defined by the claims appended hereto.

What is claimed is:

1. A gas outlet extender for use with a primary gas outlet back body, the primary gas outlet back body defining a primary port and having a primary back body plate defining a primary gas outlet aperture adapted to receive a front body gas-specific pin, the gas outlet extender comprising:
   a mounting plate defining a mounting plate aperture, the mounting plate having a first side and a second side;
   a gas outlet extender gas-specific pin mounted to the mounting plate and extending parallel to an axis of the outlet extender insertion element, to, in use, pass through the primary gas outlet aperture;
   an outlet extender insertion element, on the first side of the mounting plate, defining an insertion element channel for exchanging a flow of gas to or from the primary port of the primary gas outlet back body;
   a distributer, on the second side of the mounting plate, the distributer having a tap having a tap channel, the distributer connected to the insertion element through the mounting plate aperture and defining a distributer channel for a flow of gas between the insertion element channel and the tap channel;
   a secondary gas outlet back body defining a secondary port and having a secondary back body plate defining a secondary gas outlet aperture adapted to receive the front body gas-specific pin; and
   a connector adapted for forming a fluid connection between the tap and the secondary port in the secondary gas outlet back body.

2. The gas outlet extender of claim 1 wherein the outlet extender insertion element is cylindrical.

3. The gas outlet extender of claim 1 wherein the distributer further has a plurality of taps.

4. A gas outlet relocation assembly comprising:
   the gas outlet extender of claim 1;
   a framework;
   an outlet support arm fastened to the framework;
   the secondary gas outlet back body fastened to the outlet support arm; and
   a panel releasably fastened to the framework, the panel defining a panel aperture sized to accommodate the outlet.

5. The gas outlet relocation assembly of claim 4 wherein the connector is functionally specific to a gas that is to be carried by the connector.

6. The outlet relocation assembly of claim 5 wherein the gas is oxygen.

7. The outlet relocation assembly of claim 5 wherein the gas is nitrogen.

8. The outlet relocation assembly of claim 5 wherein the gas is medical air.

9. The outlet relocation assembly of claim 5 wherein the gas is nitrous oxide.

10. The outlet relocation assembly of claim 4 wherein the connector is visually specific to a fluid that is to be carried by the connector.

11. The outlet relocation assembly of claim 4 wherein the primary back body and front body are specific to a fluid that is supplied to the primary back body.

12. The outlet relocation assembly of claim 11 wherein the secondary back body is specific to the gas to which the primary back body is specific.

* * * * *